United States Patent
Nakamura et al.

(10) Patent No.: US 10,201,897 B2
(45) Date of Patent: Feb. 12, 2019

(54) METHOD FOR CONTROLLING ROBOT AND ROBOT SYSTEM

(71) Applicant: Kabushiki Kaisha Yaskawa Denki, Kitakyushu-shi (JP)

(72) Inventors: Miki Nakamura, Kitakyushu (JP); Yoshikazu Matsuzaki, Kitakyushu (JP)

(73) Assignee: KABUSHIKI KAISHA YASKAWA DENKI, Kitakyushu-shi (JP)

( * ) Notice: Subject to any disclaimer, the term of this patent is extended or adjusted under 35 U.S.C. 154(b) by 186 days.

(21) Appl. No.: 15/275,961

(22) Filed: Sep. 26, 2016

(65) Prior Publication Data

US 2017/0087723 A1 Mar. 30, 2017

(30) Foreign Application Priority Data

Sep. 25, 2015 (JP) .................................. 2015-188945

(51) Int. Cl.
*B25J 9/16* (2006.01)
*B25J 9/00* (2006.01)
(Continued)

(52) U.S. Cl.
CPC ........... *B25J 9/1682* (2013.01); *B25J 9/0087* (2013.01); *G01N 35/0099* (2013.01);
(Continued)

(58) Field of Classification Search
CPC ... B25J 9/1682; B25J 9/0087; G01N 35/0099; G01N 35/10; G01N 2035/1058;
(Continued)

(56) References Cited

U.S. PATENT DOCUMENTS

| 5,443,791 A | * | 8/1995 | Cathcart | ............. | B01L 3/50825 |
| | | | | | 422/561 |
| 2007/0180935 A1 | * | 8/2007 | Angus | ................... | B01L 3/0279 |
| | | | | | 73/864.14 |

(Continued)

FOREIGN PATENT DOCUMENTS

| DE | 199 00 347 A1 | 7/2000 |
| EP | 2 458 387 A2 | 5/2012 |

(Continued)

OTHER PUBLICATIONS

Extended European Search Report dated Feb. 17, 2017 in Patent Application No. 16187338.5.

(Continued)

*Primary Examiner* — Jaime Figueroa
(74) *Attorney, Agent, or Firm* — Oblon, McClelland, Maier & Neustadt, L.L.P.

(57) ABSTRACT

A method for controlling a robot includes a first step and a second step. In the first step, the robot is controlled to hold at least one of a pipette and a container containing a liquid and to change a position of the pipette relative to the container so as to make a tip of the pipette contact a sediment in the container. In the second step, the robot is controlled to move the pipette in an upward direction from a predetermined position in the container with the tip of the pipette in contact with an inner side surface of the container.

20 Claims, 8 Drawing Sheets

(51) Int. Cl.
*G01N 35/10* (2006.01)
*G01N 35/00* (2006.01)
*G01N 1/38* (2006.01)
*B01L 3/02* (2006.01)

(52) U.S. Cl.
CPC ............ *G01N 35/10* (2013.01); *B01L 3/0237* (2013.01); *G01N 1/38* (2013.01); *G01N 2035/00534* (2013.01); *G01N 2035/1018* (2013.01); *G01N 2035/1025* (2013.01); *G01N 2035/1058* (2013.01); *G05B 2219/39109* (2013.01)

(58) Field of Classification Search
CPC . G01N 2035/00534; G01N 2035/1018; G01N 2035/1025; G01N 1/38; G05B 2219/39109; B01L 3/0237
USPC ......................................................... 700/245
See application file for complete search history.

(56) References Cited

U.S. PATENT DOCUMENTS

| | | | | |
|---|---|---|---|---|
| 2008/0254545 A1* | 10/2008 | Kitaoka | ............. | G01N 35/0099 436/47 |
| 2009/0280572 A1* | 11/2009 | Ribeiro | ................ | G01N 35/025 436/164 |
| 2009/0298129 A1* | 12/2009 | Spence | ................... | B01L 3/021 435/91.2 |
| 2012/0134896 A1* | 5/2012 | Chiyajo | ............. | G01N 35/0099 422/549 |
| 2012/0214175 A1* | 8/2012 | Graham | ........... | G01N 33/54326 435/7.25 |
| 2014/0106386 A1* | 4/2014 | Umeno | ............. | G01N 35/0099 435/23 |
| 2014/0219887 A1* | 8/2014 | Sheldon | ................ | B01L 3/0279 422/509 |
| 2015/0059149 A1* | 3/2015 | Miyauchi | .............. | B01L 3/0275 29/428 |
| 2015/0127157 A1* | 5/2015 | Matsukuma | ........... | B25J 9/1682 700/258 |

FOREIGN PATENT DOCUMENTS

| | | |
|---|---|---|
| EP | 2 875 912 A1 | 5/2015 |
| JP | 2015-85490 A | 5/2015 |
| WO | WO 91/16675 A1 | 10/1991 |

OTHER PUBLICATIONS

R Daniel Gietz et al. "High-efficiency yeast transformation using the LiAc/SS carrier DNA/PEG method", Nature Protocols, vol. 2, No. 1, XP055344705, Jan. 31, 2007, pp. 31-34.

* cited by examiner

METHOD FOR CONTROLLING ROBOT AND ROBOT SYSTEM

CROSS-REFERENCE TO RELATED APPLICATIONS

The present application claims priority under 35 U.S.C. § 119 to Japanese Patent Application No. 2015-188945, filed Sep. 25, 2015. The contents of this application are incorporated herein by reference in their entirety.

BACKGROUND

Field of the Invention

The embodiments disclosed herein relate to a method for controlling a robot and relate to a robot system.

Discussion of the Background

Japanese Unexamined Patent Application Publication No. 2015-85490 discloses a robot to perform operations such as pre-analysis treatment in biomedical fields.

SUMMARY

According to one aspect of the present disclosure, a method for controlling a robot includes a first step and a second step. In the first step, the robot is controlled to hold at least one of a pipette and a container containing a liquid and to change a position of the pipette relative to the container so as to make a tip of the pipette contact a sediment in the container. In the second step, the robot is controlled to move the pipette in an upward direction from a predetermined position in the container with the tip of the pipette in contact with an inner side surface of the container.

According to another aspect of the present disclosure, a robot system includes a robot and a controller. The robot is configured to hold at least one of a pipette and a container containing a liquid. The controller is configured to control the robot, and includes a first controller and a second controller. The first controller is configured to control the robot to hold at least one of the pipette and the container and to change a position of the pipette relative to the container so as to make a tip of the pipette contact a sediment in the container. The second controller is configured to control the robot to move the pipette in an upward direction from a predetermined position in the container with the tip of the pipette in contact with an inner side surface of the container.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein.

DESCRIPTION OF THE EMBODIMENTS

Figure 1:
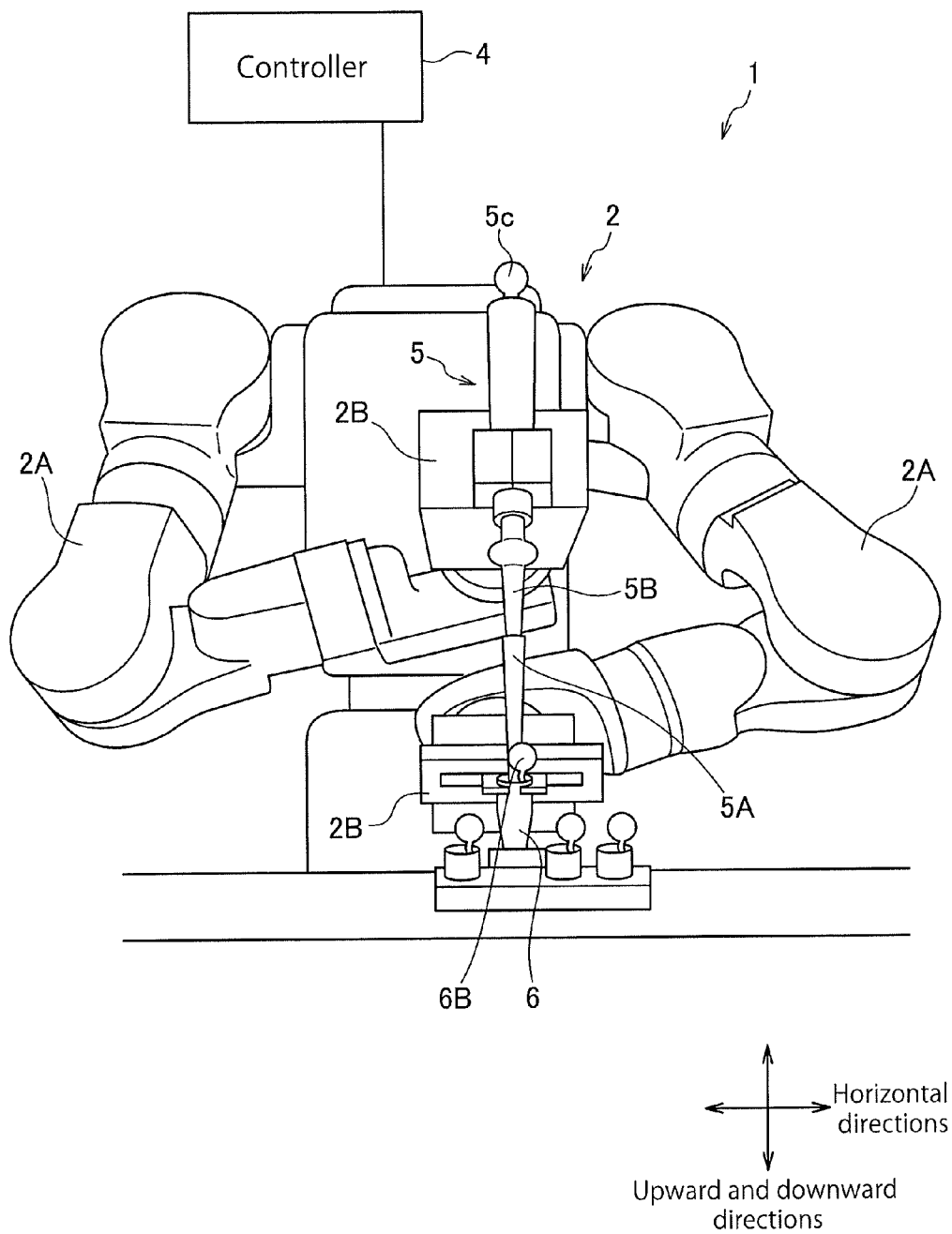
FIG. 1 is a schematic illustrating an exemplary overall configuration of a robot system according to an embodiment.

The embodiments will now be described with reference to the accompanying drawings, wherein like reference numerals designate corresponding or identical elements throughout the various drawings.

Robot System

Figure 2:
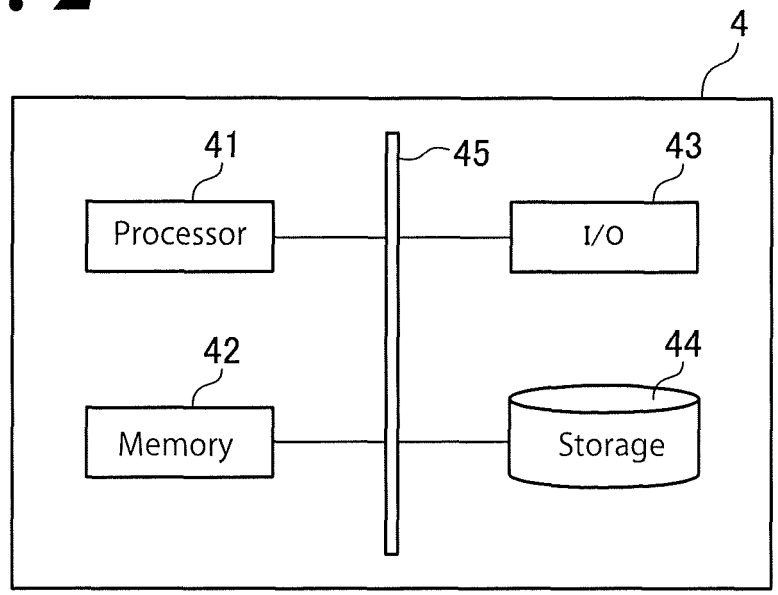
FIG. 2 illustrates an exemplary configuration of a controller according to the embodiment.

By referring to FIGS. 1 to 3, an exemplary overall configuration of a robot system 1 according to this embodiment will be described. For convenience of description of the robot system 1 and other and related elements, directions indicated by "upward and downward directions" and "horizontal direction" are indicated in FIG. 1. It should be noted, however, that these directions may vary depending on where to install the robot system 1 and other and related elements, and should not be construed as limiting their positions in relation to each other.

As illustrated in FIG. 1, the robot system 1 according to this embodiment includes a robot 2 and a controller 4. The controller 4 controls the robot 2. The robot system 1 according to this embodiment is capable of controlling the robot 2 to perform predetermined kinds of work (bench work) to treat specimens such as blood, spinal fluid, urine, and parts of tissue in biomedical fields. Examples of the bench work include, but are not limited to, adding reagent to the specimens, agitating the specimens, separating the specimens, removing supernatant off the specimens, heating the specimens, and cooling the specimens.

In the following description, the bench work that the robot system 1 according to this embodiment controls the robot 2 to perform is "pipetting". In the pipetting, the robot 2 uses a pipette 5 (a non-limiting example of which is a micro-pipette) to measure a precise amount of liquid contained in a container 6 (a non-limiting example of which is a micro-tube), take the amount of liquid out of the container 6, and put the amount of liquid into another container.

As illustrated in FIG. 1, the robot 2 includes right and left arms 2A. Each of the arms 2A includes a hand 2B at the leading end of each arm 2A. The hand 2B is capable of holding objects such as the pipette 5 and the container 6, which contains liquid 10. In the embodiment of FIG. 1, the robot 2 is a two-arm robot with two multi-articular arms, namely, the arms 2A.

The pipette 5 is a treatment instrument generally referred to as a pipette or a micro-pipette, which is used to suck and inject reagent or supernatant, as generally known. The pipette 5 includes a tip (nozzle) 5A, a body 5B, and a tail 5C. By pinching the tail 5C, air is discharged through the tip 5A, making the internal pressure of the pipette 5 negative enough to allow liquid into the body 5B.

The container 6 is generally referred to as a tube or a micro-tube, and includes a lid 6B. The following description of this embodiment will be under the assumption that the container 6 contains the liquid 10. Examples of the liquid 10 include, but are not limited to, reagent and supernatant.

As illustrated in FIG. 1, the controller 4 controls the robot 2. For example, as illustrated in FIG. 2, the controller 4 includes a processor 41, a memory 42, an input/output section (I/O) 43, a storage 44, and a bus 45. The bus 45 connects the processor 41, the memory 42, the input/output section (I/O) 43, and the storage 44 to each other. The processor 41 cooperates with at least one of the memory 42 and the storage 44 to execute a program, and uses a result of executing the program as a basis for inputting and outputting data through the input/output section 43. In this manner, the controller 4 implements various functions. FIG. 3 illustrates these functions in the form of imaginary blocks (hereinafter referred to as functional blocks).

Figure 3:
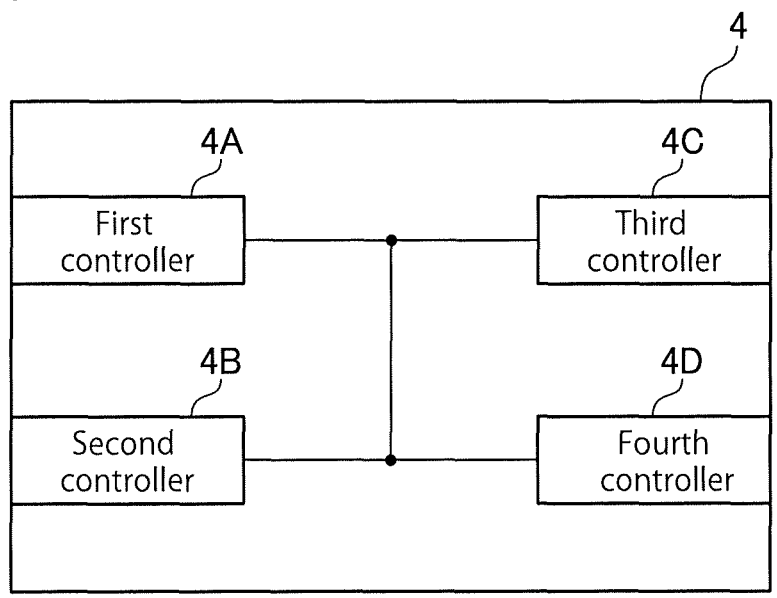
FIG. 3 illustrates an exemplary functional configuration of the controller according to the embodiment.

As illustrated in FIG. 3, the functional blocks of the controller 4 are a first controller 4A, a second controller 4B, a third controller 4C, and a fourth controller 4D.

The first controller 4A controls the robot 2 to hold at least one of the container 6 and the pipette 5 and to change the position of the pipette 5 relative to the container 6 so as to make the tip 5A of the pipette 5 contact the sediment 20 in the container 6 (in other words, so as to control the robot 2 to perform "sediment diffusion operation").

In the embodiment of FIG. 1, the pipette 5 is held by the hand 2B disposed at the leading end of the right arm 2A of the robot 2, and the container 6 is held by the hand 2B disposed at the leading end of the left arm 2A of the robot 2. This configuration, however, is not intended as limiting the configuration of the robot system 1.

The first controller 4A may control the robot 2 to hold the container 6 using either the right arm 2A or the left arm 2A so as to perform the above-described sediment diffusion operation (or sediment removal operation, described later). In this case, the pipette 5 is held by a predetermined device.

Alternatively, the first controller 4A may control the robot 2 to hold the pipette 5 using either the right arm 2A or the left arm 2A so as to perform the above-described sediment diffusion operation (or the sediment removal operation, described later). In this case, the container 6 is held by the above-described predetermined device or another predetermined device.

The sediment 20 occurs as a result of the above-described bench work. In some cases, the sediment 20 has a viscosity high enough to attach to the bottom of the container 6, the inner side surface, 6A, of the container 6, or somewhere else in the container 6. In other cases, the sediment 20 accumulates on the bottom of the container 6 or somewhere else in the container 6. When the sediment 20 is attached to the bottom of the container 6, the inner side surface 6A of the container 6, or somewhere else in the container 6, the first controller 4A may control the robot 2 to change the position of the pipette 5 relative to the container 6 so as to make the tip 5A contact and break the sediment 20 attached to the bottom of the container 6, the inner side surface 6A of the container 6, or somewhere else in the container 6.

For example, the first controller 4A may control the robot 2 to recognize the position of the sediment 20 in the container 6 using image recognition technology and to change the position of the pipette 5 relative to the container 6 by moving the pipette 5 toward the recognized position so as to make the tip 5A contact the sediment 20 in the container 6. Alternatively, the first controller 4A may control the robot 2 to change the position of the pipette 5 relative to the container 6 by moving the pipette 5 toward one predetermined position or a plurality of predetermined positions so as to make the tip 5A contact the sediment 20 in the container 6.

In order to change the position of the pipette 5 relative to the container 6 and to make the tip 5A contact the sediment 20 in the container 6, the first controller 4A controls the robot 2 to move the pipette 5 in the upward and downward directions. Alternatively, the first controller 4A may control the robot 2 to move the pipette 5 in direction(s) other than the upward and downward directions (for example, in the horizontal direction), in order to change the position of the pipette 5 relative to the container 6 and to make the tip 5A contact the sediment 20 in the container 6.

The second controller 4B controls the robot 2 to move the pipette 5 in the upward direction (that is, change the position of the pipette 5 relative to the container 6) from a predetermined position in the container 6 with the tip 5A in contact with the inner side surface 6A of the container 6.

This configuration enables the tip 5A to diffuse the sediment 20 over the liquid 10 in the container 6 and enables the inner side surface 6A of the container 6 to remove the sediment 20 attached to the tip 5A and diffuse the sediment 20 over the liquid 10, resulting in improved performance of the bench work.

Alternatively or simultaneously, the second controller 4B may control the robot 2 to move the pipette 5 while changing the position at which the tip 5A of the pipette 5 contacts the inner side surface 6A of the container 6 (that is, to perform the "sediment removal operation"). This configuration increases the amount of the sediment 20 removal from the tip 5A.

Specifically, the second controller 4B may control the robot 2 to turn the container 6 in the horizontal direction while moving the pipette 5 in the upward direction. This configuration makes changeable, without turning the pipette 5, the position at which the tip 5A contacts the inner side surface 6A of the container 6. This, in turn, increases the amount of the sediment 20 removal from the tip 5A.

Alternatively or simultaneously, the second controller 4B may control the robot 2 to move the pipette 5 in the upward direction while turning the pipette 5 in the horizontal direction. This configuration makes changeable, without turning the container 6, the position at which the tip 5A contacts the inner side surface 6A of the container 6. This, in turn, increases the amount of the sediment 20 removal from the tip 5A.

Alternatively or simultaneously, the first controller 4A may control the robot 2 to perform the sediment diffusion operation a plurality of times each at a different position at which the tip 5A contacts the sediment 20, and the second controller 4B may control the robot 2 to perform the sediment removal operation a plurality of times each from a different predetermined position. This configuration improves reliability in removing the sediment 20 attached to the tip 5A.

In performing the sediment removal operation a plurality of times, the second controller 4B may control the robot 2 to take the tip 5A out of the liquid 10 at least once and to put the tip 5A back into the liquid 10. The second controller 4B may control the robot 2 to perform the sediment removal operation a predetermined number of times, to take the tip 5A out of the liquid 10, to put the tip 5A back into the liquid 10, and to perform the rest of the sediment removal operations (see FIGS. 8 and 9, described later). This configuration utilizes the surface tension of the surface of the liquid 10 and improves efficiency in removing the sediment 20 attached to the tip 5A.

The third controller 4C may control the robot 2 to diffuse the sediment 20 over the liquid 10 and to stir the liquid 10 using the pipette 5. This configuration improves reliability in diffusing the sediment 20 over the liquid 10.

After the sediment removal operation(s), the fourth controller 4D controls the robot 2 to press the tail 5C of the pipette 5 at a first speed. Then, the fourth controller 4D controls the robot 2 to press the tail 5C of the pipette 5 at a second speed higher than the first speed so as to perform stirring operation (suspending operation). This configuration eliminates or minimizes clogging 30 of the tip 5A before the stirring operation is performed.

Method for Controlling Robot

By referring to FIGS. 4 to 10, an exemplary method for controlling the robot 2 performed by the controller 4 will be described. The method according to this embodiment for controlling the robot 2 is a method for performing the above-described bench work.

Figure 4:
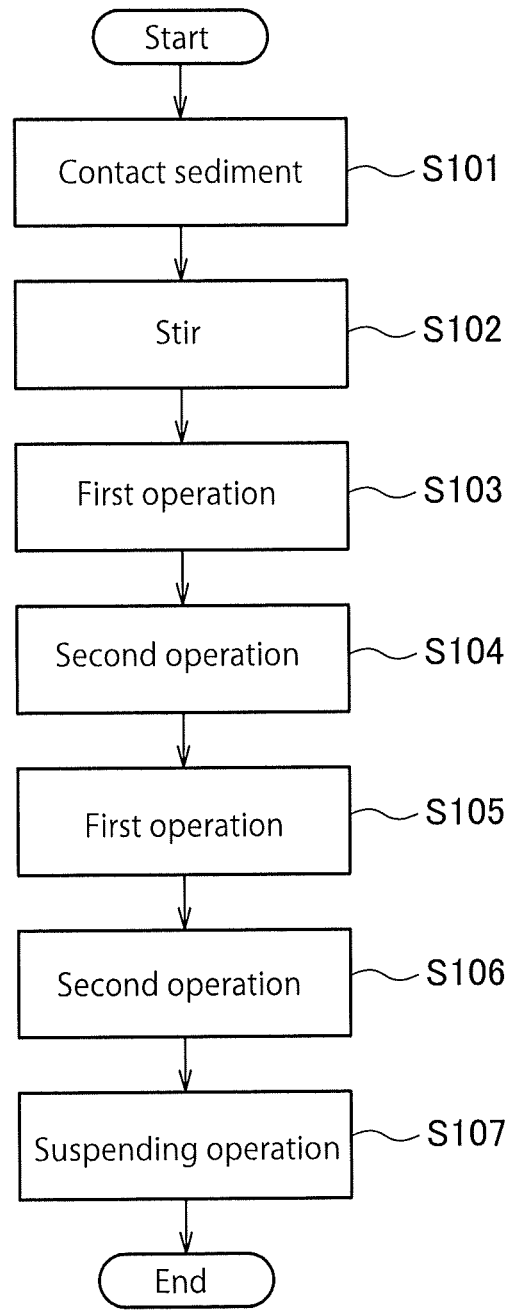
FIG. 4 is an exemplary flowchart of a method according to an embodiment for controlling a robot.
Figure 5:
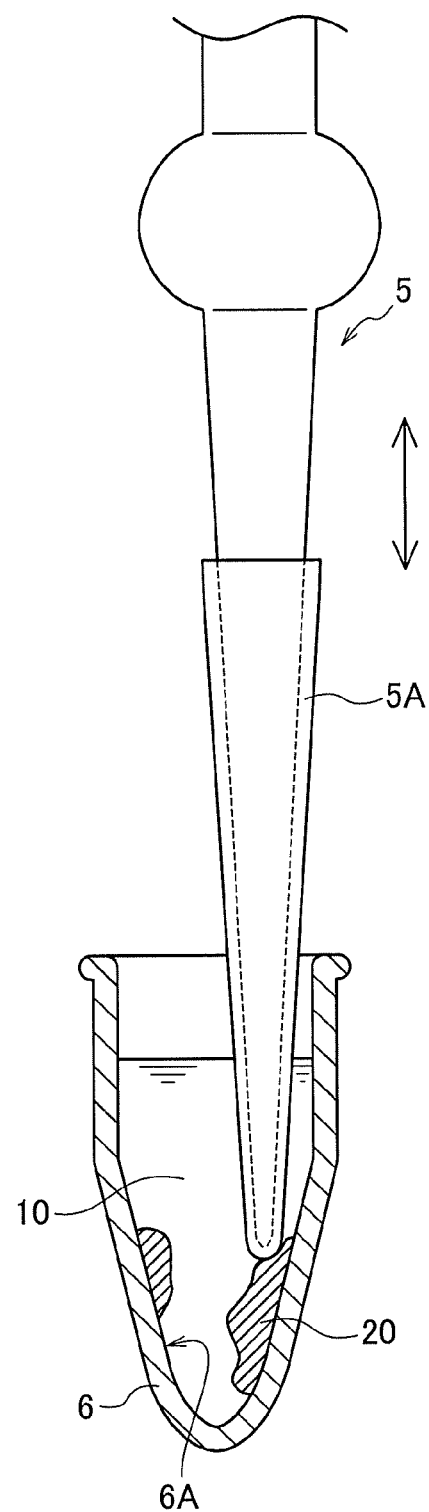
FIG. 5 illustrates an example of how a robot system according to an embodiment operates.

As illustrated in FIG. 4, at step S101, the controller 4 controls the robot 2 to hold at least one of the container 6 and the pipette 5 and to change the position of the pipette 5 relative to the container 6 so as to make the tip 5A of the pipette 5 contact the sediment 20 in the container 6. For example, as illustrated in FIG. 5, the controller 4 controls the robot 2 to move the pipette 5 in the upward and downward directions so as to change the position of the pipette 5 relative to the container 6 and to make the tip 5A of the pipette 5 contact the sediment 20 in the container 6.

Figure 6:
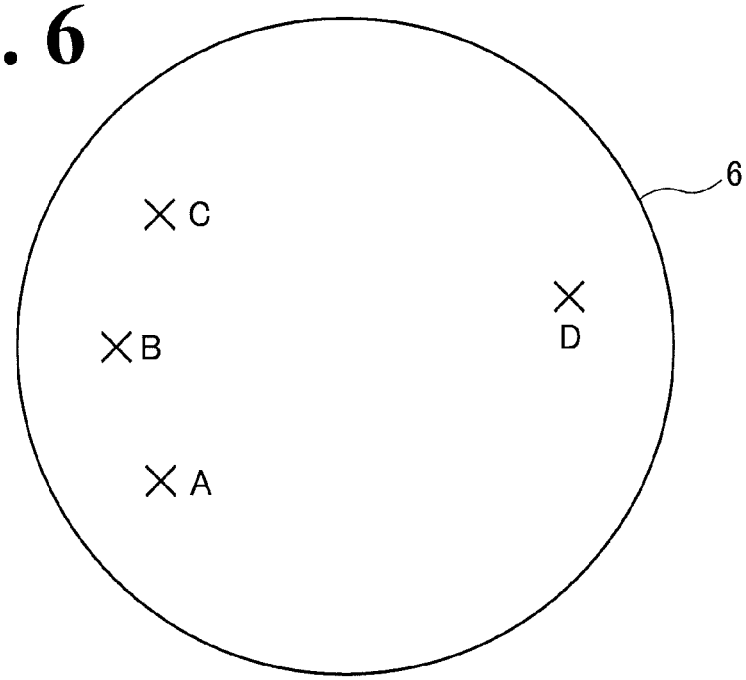
FIG. 6 illustrates another example of how the robot system according to the embodiment operates.

The controller 4 controls the robot 2 to perform the sediment diffusion operation a plurality of times each at a different position at which the tip 5A contacts the sediment 20. For example, as illustrated in FIG. 6, the controller 4 may control the robot 2 to make the tip 5A of the pipette 5 contact the sediment 20 at four positions, namely, "A", "B", "C", and "D", so as to diffuse the sediment 20 over the liquid 10.

Figure 7:
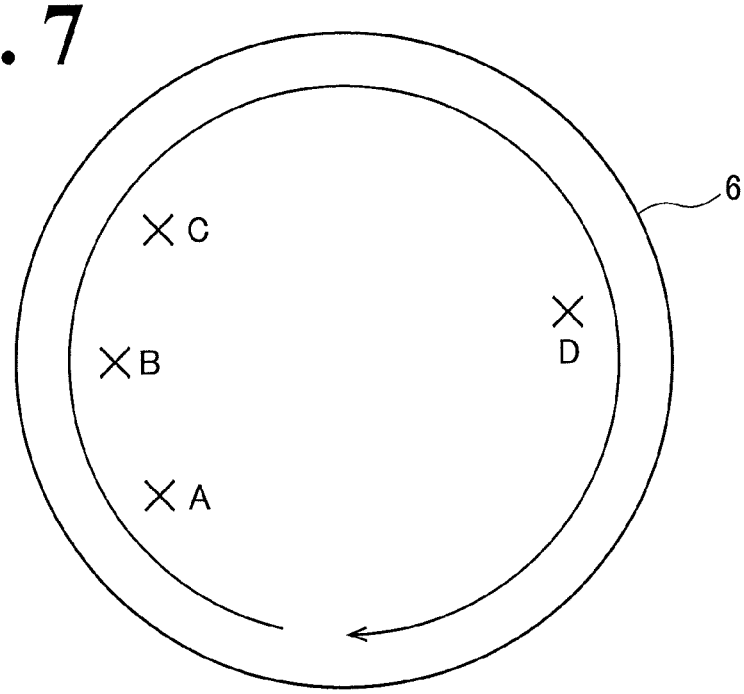
FIG. 7 illustrates another example of how the robot system according to the embodiment operates.

At step S102, the controller 4 controls the robot 2 to stir the liquid 10 using the pipette 5. For example, as illustrated in FIG. 7, the controller 4 may control the robot 2 to cause the pipette 5 (tip 5A) to make two revolutions in the horizontal direction so as to stir the liquid 10. In the embodiment of FIG. 7, the controller 4 controls the robot 2 to turn the pipette 5 (tip 5A) clockwise in the horizontal direction. In another possible embodiment, the controller 4 may control the robot 2 to turn the pipette 5 (tip 5A) anti-clockwise in the horizontal direction.

At step S103, the controller 4 controls the robot 2 to perform "first operation". At step S104, the controller 4 controls the robot 2 to perform "second operation". At step S105, the controller 4 controls the robot 2 to perform the "first operation". At step S106, the controller 4 controls the robot 2 to perform the "second operation".

By referring to FIGS. 8 and 9, the "first operation" and the "second operation" illustrated in FIG. 4 will be described. The "first operation" and the "second operation" are among the sediment diffusion operation performed a plurality of times.

By referring to FIGS. 8A, 8B, 8C, 8D, and 8E, the "first operation" will be described. First, the tip 5A moves in the downward direction while keeping contact with the inner side surface 6A of the container 6 (see FIGS. 8A and 8B). Second, the tip 5A moves in the upward direction while keeping contact with the inner side surface 6A. At the same time, the container 6 turns anti-clockwise in the horizontal direction (see FIG. 8C). Third, the tip 5A moves in the downward direction while keeping contact with the inner side surface 6A. At the same time, the container 6 turns clockwise in the horizontal direction (see FIG. 8D). Fourth, the tip 5A moves in the upward direction while keeping contact with the inner side surface 6A. At the same time, the container 6 turns anti-clockwise in the horizontal direction (see FIG. 8E).

Figure 8A:
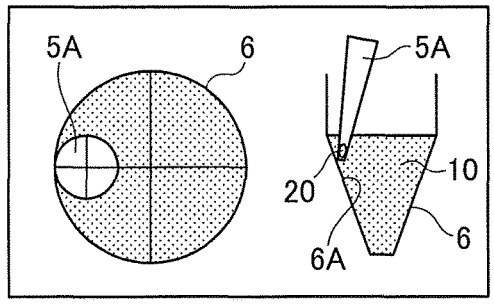
FIGS. 8A, 8B, 8C, 8D, and 8E illustrate another example of how the robot system according to the embodiment operates.
Figure 8D:
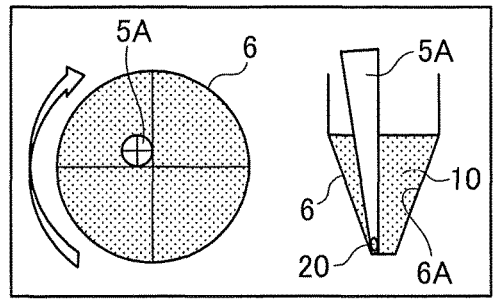
Figure 8B:
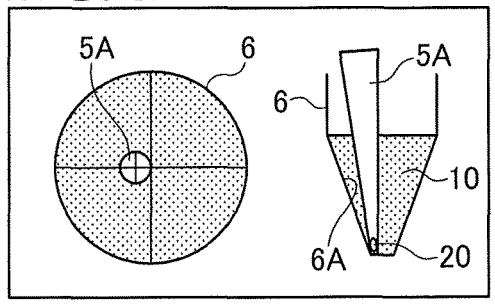
Figure 8E:
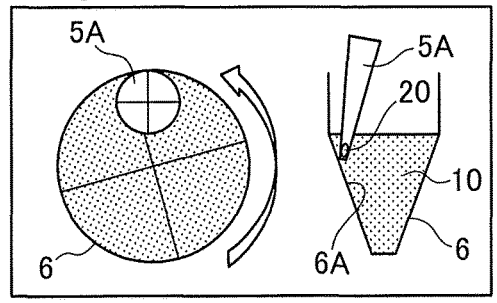
Figure 8C:
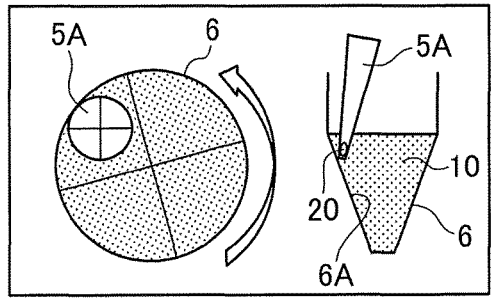

These operations are repeated until the position at which the tip 5A contacts the inner side surface 6A of the container 6 has moved to a position 180° (degrees) away from the position illustrated in FIG. 8A.

By referring to FIGS. 9A, 9B, 9C, 9D, 9E, and 9F, the "second operation" will be described. First, the tip 5A moves in the downward direction while keeping contact with the inner side surface 6A (see FIG. 9A). Second, the tip 5A moves in the upward direction while keeping contact with the inner side surface 6A. At the same time, the container 6 turns clockwise in the horizontal direction (see FIG. 9B). Third, the tip 5A is removed out of the liquid 10. At the same time, the container 6 turns anti-clockwise in the horizontal direction (see FIG. 9C).

Figure 9A:
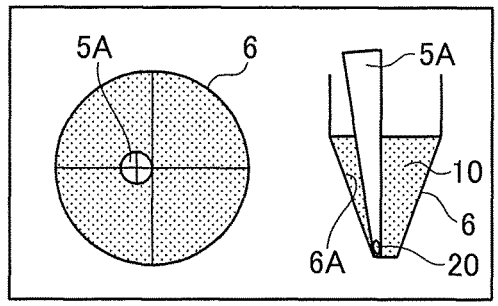
FIGS. 9A, 9B, 9C, 9D, 9E, and 9F illustrate another example of how the robot system according to the embodiment operates.
Figure 9D:
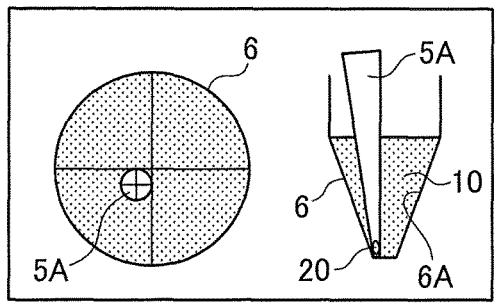
Figure 9B:
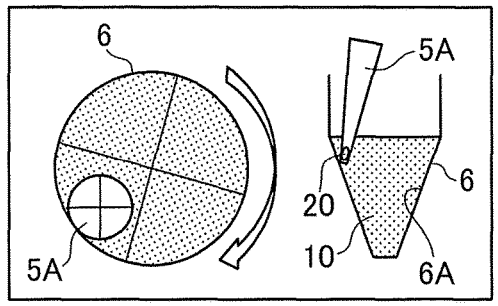
Figure 9E:
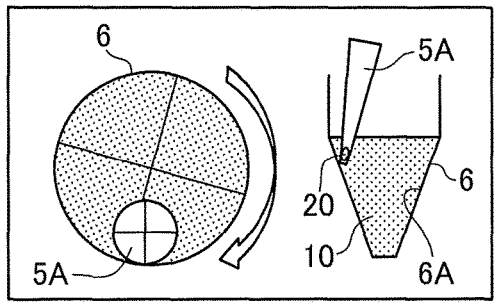
Figure 9C:
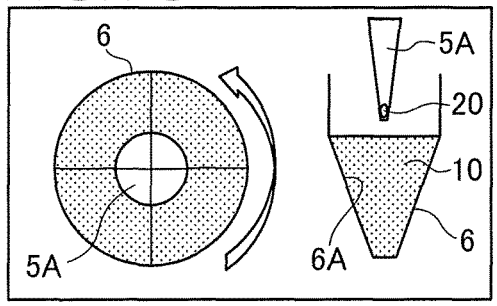
Figure 9F:
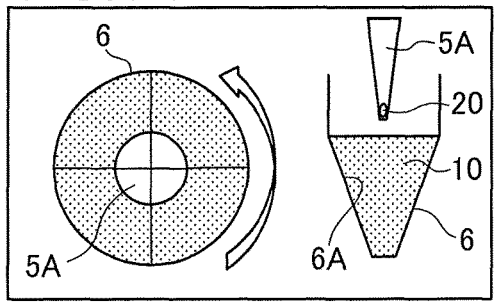

Fourth, the tip 5A is put back into the liquid 10 and moves in the downward direction while keeping contact with the inner side surface 6A (see FIG. 9D). Fifth, the tip 5A moves in the upward direction while keeping contact with the inner side surface 6A. At the same time, the container 6 turns clockwise in the horizontal direction (see FIG. 9E). Sixth, the tip 5A is removed out of the liquid 10. At the same time, the container 6 turns anti-clockwise in the horizontal direction (see FIG. 9F).

These operations are repeated until the position at which the tip 5A contacts the inner side surface 6A of the container 6 has moved to a position 180° away from the position illustrated in FIG. 9A.

Figure 10:
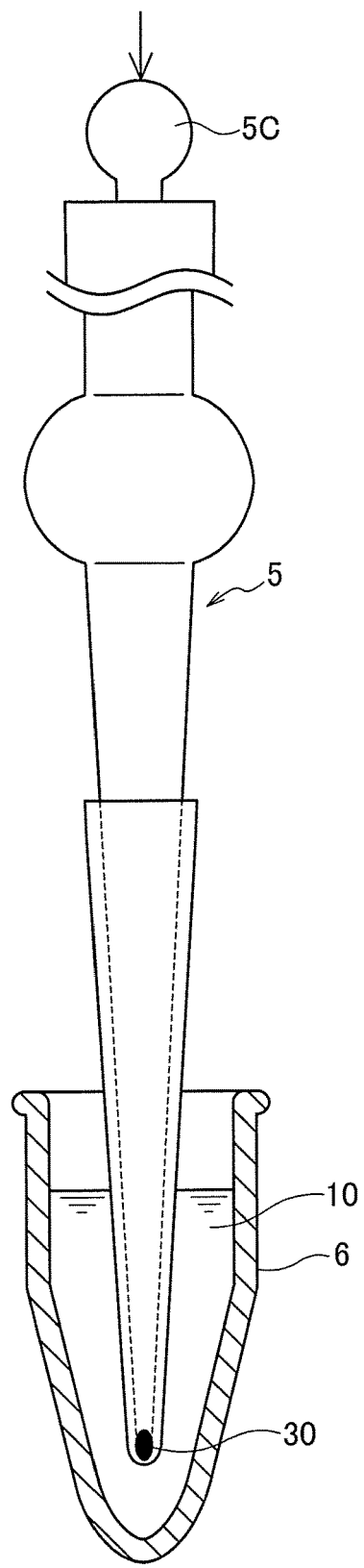
FIG. 10 illustrates another example of how the robot system according to the embodiment operates.

At step S107, illustrated in FIG. 10, the controller 4 controls the robot 2 to press the tail 5C of the pipette 5 at the first speed and then to press the tail 5C of the pipette 5 at the second speed, which is higher than the first speed, so as to perform the stirring operation (suspending operation).

Thus, even when the robot 2 performs predetermined work such as pre-analysis treatment, the robot system 1 according to this embodiment and the method according to this embodiment for controlling a robot reduce the sediment 20 in the container 6 and thus improve performance of the predetermined work.

Obviously, numerous modifications and error of the present disclosure are possible in light of the above teachings. It is therefore to be understood that within the scope of the appended claims, the present disclosure may be practiced otherwise than as specifically described herein.

The invention claimed is:

1. A method for controlling a robot, comprising:
controlling a robot such that the robot holds at least one of a pipette and a container containing a liquid;
controlling the robot holding at least one of the pipette and the container such that the robot makes a tip of the pipette contact with a sediment in the container by changing a position of the pipette relative to the container; and
controlling the robot holding at least one of the pipette and the container such that after making the tip of the pipette contact with the sediment in the container, the robot moves the pipette in an upward direction relative to the container from a position in the container with the tip of the pipette in contact with an inner side surface of the container while keeping the tip of the pipette in contact with the inner side surface of the container.

2. The method according to claim 1, further comprising:
controlling the robot holding at least one of the pipette and the container such that the pipette diffuses the sediment in the liquid; and
controlling the robot holding at least one of the pipette and the container such that the pipette stirs the liquid in the container.

3. The method according to claim 1, wherein the controlling to move the pipette in the upward direction comprises controlling the robot holding at least one of the pipette and the container such that the robot moves the pipette in the upward direction relative to the container while changing a position in which the tip of the pipette is in contact with the inner side surface of the container.

4. The method according to claim 3, wherein the controlling to move the pipette in the upward direction comprises controlling the robot holding at least one of the pipette and the container such that the robot turns the container in a horizontal direction while moving the pipette in the upward direction.

5. The method according to claim 3, wherein the controlling to move the pipette in the upward direction comprises controlling the robot holding at least one of the pipette and the container such that the robot moves the pipette in the upward direction relative to the container while turning the pipette in a horizontal direction.

6. The method according to claim 1, further comprising:
controlling the robot holding at least one of the pipette and the container such that the robot changes a position of the pipette relative to the container;
controlling the robot holding at least one of the pipette and the container such that the robot makes the tip of the pipette contact with the sediment in the container at a different position; and
controlling the robot holding at least one of the pipette and the container such that the robot moves the pipette in the upward direction from a different position in the container with the tip of the pipette in contact with the inner side surface of the container.

7. The method according to claim 6, further comprising:
controlling the robot holding at least one of the pipette and the container such that the robot takes the tip of the pipette out of the liquid at least once and put the tip of the pipette back into the liquid when the robot moves the pipette in the upward direction.

8. The method according to claim 6, further comprising:
setting a number of times in which the robot makes the tip of the pipette contact with the sediment in the container by changing the position of the pipette relative to the container; and
controlling the robot holding at least one of the pipette and the container such that the robot takes the tip of the pipette out of the liquid at least once and put the tip of the pipette back into the liquid when the robot moves the pipette in the upward direction.

9. The method according to claim 1, further comprising:
controlling the robot holding at least one of the pipette and the container such that the robot presses and moves a tail of the pipette at a first speed in a stirring operation; and
controlling the robot holding at least one of the pipette and the container such that the robot presses and moves the tail of the pipette at a second speed higher than the first speed in the stirring operation.

10. The method according to claim 2, wherein the controlling to move the pipette in the upward direction comprises controlling the robot holding at least one of the pipette and the container such that the robot moves the pipette in the upward direction relative to the container while changing a position in which the tip of the pipette is in contact with the inner side surface of the container.

11. The method according to claim 10, wherein the controlling to move the pipette in the upward direction comprises controlling the robot holding at least one of the pipette and the container such that the robot turns the container in a horizontal direction while moving the pipette in the upward direction.

12. The method according to claim 10, wherein the controlling to move the pipette in the upward direction comprises controlling the robot holding at least one of the pipette and the container such that the robot moves the pipette in the upward direction relative to the container while turning the pipette in a horizontal direction.

13. The method according to claim 2, further comprising:
controlling the robot holding at least one of the pipette and the container such that the robot changes a position of the pipette relative to the container;
controlling the robot holding at least one of the pipette and the container such that the robot makes the tip of the pipette contact with the sediment in the container at a different position; and
controlling the robot holding at least one of the pipette and the container such that the robot moves the pipette in the upward direction from a different position in the container with the tip of the pipette in contact with the inner side surface of the container.

14. The method according to claim 3, further comprising:
controlling the robot holding at least one of the pipette and the container such that the robot changes a position of the pipette relative to the container;
controlling the robot holding at least one of the pipette and the container such that the robot makes the tip of the pipette contact with the sediment in the container at a different position; and
controlling the robot holding at least one of the pipette and the container such that the robot moves the pipette in the upward direction from a different position in the container with the tip of the pipette in contact with the inner side surface of the container.

15. The method according to claim 4, further comprising:
controlling the robot holding at least one of the pipette and the container such that the robot changes a position of the pipette relative to the container;
controlling the robot holding at least one of the pipette and the container such that the robot makes the tip of the pipette contact with the sediment in the container at a different position; and
controlling the robot holding at least one of the pipette and the container such that the robot moves the pipette in the upward direction from a different position in the container with the tip of the pipette in contact with the inner side surface of the container.

16. The method according to claim 5, further comprising:
controlling the robot holding at least one of the pipette and the container such that the robot changes a position of the pipette relative to the container;
controlling the robot holding at least one of the pipette and the container such that the robot makes the tip of the pipette contact with the sediment in the container at a different position; and
controlling the robot holding at least one of the pipette and the container such that the robot moves the pipette in the upward direction from a different position in the container with the tip of the pipette in contact with the inner side surface of the container.

17. The method according to claim 10, further comprising:
controlling the robot holding at least one of the pipette and the container such that the robot changes a position of the pipette relative to the container;
controlling the robot holding at least one of the pipette and the container such that the robot makes the tip of the pipette contact with the sediment in the container at a different position; and
controlling the robot holding at least one of the pipette and the container such that the robot moves the pipette in the upward direction from a different position in the container with the tip of the pipette in contact with the inner side surface of the container.

18. The method according to claim 11, further comprising:
controlling the robot holding at least one of the pipette and the container such that the robot changes a position of the pipette relative to the container;
controlling the robot holding at least one of the pipette and the container such that the robot makes the tip of the pipette contact with the sediment in the container at a different position; and
controlling the robot holding at least one of the pipette and the container such that the robot moves the pipette in the upward direction from a different position in the container with the tip of the pipette in contact with the inner side surface of the container.

19. The method according to claim 12, further comprising:
controlling the robot holding at least one of the pipette and the container such that the robot changes a position of the pipette relative to the container;
controlling the robot holding at least one of the pipette and the container such that the robot makes the tip of the pipette contact with the sediment in the container at a different position; and
controlling the robot holding at least one of the pipette and the container such that the robot moves the pipette in the upward direction from a different position in the container with the tip of the pipette in contact with the inner side surface of the container.

20. A robot system, comprising:
a robot configured to hold at least one of a pipette and a container containing a liquid; and
a controller comprising circuitry configured to control the robot such that the robot holds at least one of the pipette and the container, makes a tip of the pipette contact a sediment in the container by changing a position of the pipette relative to the container, and after making the tip of the pipette contact with the sediment in the container, moves the pipette in an upward direction relative to the container from a position in the container with the tip of the pipette in contact with an inner side surface of the container while keeping the tip of the pipette in contact with the inner side surface of the container.

* * * * *